United States Patent
Neumann et al.

(10) Patent No.: US 11,275,028 B2
(45) Date of Patent: Mar. 15, 2022

(54) RAPID CULTURE FREE PATHOGEN DETECTION VIA OPTICAL SPECTROSCOPY

(71) Applicants: Aaron Kurt Neumann, Albuquerque, NM (US); Anatoliy O Pinchuk, Colorado Springs, CO (US); Ke Jiang, Colorado Springs, CO (US)

(72) Inventors: Aaron Kurt Neumann, Albuquerque, NM (US); Anatoliy O Pinchuk, Colorado Springs, CO (US); Ke Jiang, Colorado Springs, CO (US)

(73) Assignee: STC.UNM, Albuquerque, NM (US)

( * ) Notice: Subject to any disclaimer, the term of this patent is extended or adjusted under 35 U.S.C. 154(b) by 266 days.

(21) Appl. No.: 16/333,681

(22) PCT Filed: Sep. 18, 2017

(86) PCT No.: PCT/US2017/052050
§ 371 (c)(1),
(2) Date: Mar. 15, 2019

(87) PCT Pub. No.: WO2018/053421
PCT Pub. Date: Mar. 22, 2018

(65) Prior Publication Data
US 2019/0265166 A1    Aug. 29, 2019

Related U.S. Application Data

(60) Provisional application No. 62/396,548, filed on Sep. 19, 2016.

(51) Int. Cl.
| | |
|---|---|
| *C12Q 1/00* | (2006.01) |
| *G01N 21/65* | (2006.01) |
| *C12Q 1/04* | (2006.01) |
| *G01N 33/569* | (2006.01) |
| *G01N 33/543* | (2006.01) |

(52) U.S. Cl.
CPC .............. *G01N 21/658* (2013.01); *C12Q 1/04* (2013.01); *G01N 21/65* (2013.01); *G01N 33/54373* (2013.01); *G01N 33/56911* (2013.01); *G01N 33/56961* (2013.01)

(58) Field of Classification Search
CPC ........ G01N 21/65; G01N 21/658; C12Q 1/00; C12Q 1/02; A61K 39/00
USPC ....................... 424/93.1; 435/4, 29
See application file for complete search history.

(56) References Cited

PUBLICATIONS

Cowcher et al. (Analytical Chemistry, 85:3297-3302, 2013).*
Farquharson et al. (Analyst, 139:6366-6370, 2014).*

* cited by examiner

*Primary Examiner* — Albert M Navarro
(74) *Attorney, Agent, or Firm* — Gonzales Patent Services; Ellen Gonzales

(57) ABSTRACT

Methods and apparatus for rapid, culture and/or label free pathogen detection. The methods utilize optical spectroscopy techniques to identify and/or characterize pathogens in a sample via the detection of unique properties and/or analytes that are specific to particular pathogens.

12 Claims, 6 Drawing Sheets

RAPID CULTURE FREE PATHOGEN DETECTION VIA OPTICAL SPECTROSCOPY

CROSS-REFERENCE TO RELATED APPLICATIONS

The following application is a National Stage application of PCT/US2017/052050, filed Sep. 18, 2017, which claims benefit of U.S. Provisional Application No. 62/396,548, filed Sep. 19, 2016 both of which are hereby incorporated by reference in its entirety.

BACKGROUND

There is an urgent need for rapid, culture-free diagnostics for infectious disease. Most diagnostic methods are hampered by the need for a microbiological culture step, which causes a delay of at least 24-48 hours before the organism is identified. In patients with septic shock, significant immune compromise and meningitis, treatment delay is unacceptable as it leads to high mortality. These patients require initiation of antimicrobial therapy within hours. At present, empiric antimicrobial therapy is provided well before the pathogen is known. Rapid identification (i.e., within hours) of even the general class of pathogen would direct therapy toward an appropriate target at an earlier stage, save lives and improve health outcomes.

As a specific example, cancer patients receiving cytotoxic antineoplastic therapies are at high risk for infection due to neutropenic status, which compromises innate immune inflammatory responses, and frequent occurrence of mucositis, which allows translocation of pathogens across mucosal surfaces. 70% of these patients require emergent care and ~23% of those present with fever/febrile neutropenia[1]. Empiric antimicrobial therapy should be initiated within an hour of triage, and each hour of delay is associated with an 18% increase in mortality[2,3]. *Pseudomonas aeruginosa, Staphylococcus aureus* and *Candida albicans* are all common causes of febrile neutropenia, each requiring different antibiotics for appropriate coverage.

*Candida* species are commensal pathogens that usually reside on mucosal surfaces. If given the opportunity, the fungus will transition from a commensal organism to become a pathogen which can create infections that range from superficial to systemic. *Candida* species are the most common fungal pathogens with *C. albicans* arising the most often followed by *C. glabrata* and *C. parapsilosis*, respectively[35,36,37,38]. Not only is there a high mortality rate associated with candidiasis, but there is also a healthcare cost that can exceed billions of dollars annually[35,39,40,41].

In order to reduce mortality associated with fungal infections, early and accurate identification are essential. Studies have shown that late diagnosis and incorrect diagnosis of *Candida* species leads to a significant increase in mortality[42,43]. There are multiple clinical diagnostic methods used to support candidiasis diagnoses. Regardless of the detection method (e.g., mass spectrometry, PCR), a microbiological culture step is usually required prior to pathogen identification. This culture step can take between 2-5 days from receipt of a clinical sample (e.g., blood, catheter tip, sputum, urine) to microbiological identification. This long time-to-identification can lead to delays in initiation of optimal antimicrobial chemotherapy. Previous studies have shown relatively poor sensitivity of clinical diagnostics for candidiasis, with a 30-50% false negative rate for blood cultures in patients with autopsy-confirmed cases of candidiasis[44,45]. This demonstrates the limitations for both time and reliability of diagnosis for common existing diagnostic approaches for candidiasis.

Microbial biofilms growing on surfaces of host tissue and medical device materials play an important role in the establishment and maintenance of infections[4]. Bacteria and fungi readily form biofilms, which are often highly resistant to antimicrobial therapy and may disperse to disseminate infection.

Standard culture methods involve significant delay (>24 hours), so faster, culture-free methods are clearly needed to efficiently achieve appropriate antimicrobial therapy.

SUMMARY

The present disclosure provides various methods and apparatus for rapid, culture free pathogen detection. According to various embodiments, the methods can be performed at a point of care facility rather than at a reference laboratory and can be performed using equipment that does not require extensive training and which, in some cases may be portable. According to various embodiments, the present disclosed methods utilize optical spectroscopy techniques to identify and characterize pathogens via the detection of unique properties and/or analytes that are specific to particular pathogens.

DETAILED DESCRIPTION

The present disclosure provides various methods and apparatus for rapid, culture free pathogen detection. According to various embodiments, the present disclosed methods utilize one or more spectroscopy techniques to identify and characterize pathogens via the detection of unique properties and/or analytes that are specific to particular pathogens.

For the purposes of the present disclosure, the term "rapid" is intended to mean that pathogen detection can take place in a clinical setting on the order of minutes to hours as opposed to current methods which take place on the order of days.

For the purposes of the present disclosure, the term "culture free" is intended to mean that there is no necessary step prior to sample preparation for analysis involving microbiological culture in nutrient medium for the purpose of increasing the number of cells present in the specimen through cell division.

For the purposes of the present disclosure, the term "label free" is intended to mean the signal to be measured does not require application of exogenous substances that will be the source of signals that serve as markers of the presence or absence of the pathogen in the specimen. For instance, an example of a label would be a fluorescent dye or an enzyme/colorimetric substrate that could be detected as a signal.

According to an embodiment, the present disclosure utilizes various techniques including, but not limited to, Raman Spectroscopy (RS), or Surface Enhanced Raman Spectroscopy (SERS), to detect analytes that are specific to particular pathogens. According to a more specific embodiment, the present disclosure utilizes one or more spectroscopy techniques to detect Quorum Sensing Molecules (QSMs) that can be used as biomarkers for specific pathogens. Bacteria and fungi readily form biofilms, which are often highly resistant to antimicrobial therapy and may disperse to disseminate infection. The process of biofilm growth and dispersal is regulated by microbial soluble small molecule messengers known as QSMs. Different types of bacterial and fungal pathogens use unique classes and structures of QSMs. These QSMs relay information both within and between species boundaries, coordinating cell density-dependent genetic programs that control adhesion, motility, biofilm formation, cellular morphology, virulence, etc. *P. aeruginosa*, *S. aureus* and *C. albicans* are common causative agents of febrile neutropenia that span the spectrum of gram negative bacteria, gram positive bacteria and fungi. Their QSMs are well characterized and chemically distinct, making them potentially good biomarkers. For example, *P. aeruginosa* produces a variety of acyl homoserine lactones (AHL) and quinolone compounds that regulate biofilm formation, bacterial motility and invasiveness as well as phenazine toxins (i.e., pyocyanin)[5]. *S. aureus* relies on autoinducing peptides (AIP), which are short peptides with a thiolactone ring modification that promote acquisition of virulence traits[6]. *C. albicans* secretes the small organic alcohol QSMs farnesol and tyrosol, which regulate the yeast to hyphal morphological transition that is key to tissue invasion[7,8].

According to the present disclosure, a second method for QSM biomarker detection utilizes Raman Spectroscopy (RS) and/or Surface Enhanced Raman Spectroscopy (SERS). Raman spectroscopy and microscopy afford facile identification of biomolecules in complex chemical environment[9-11]. In SERS, Raman Spectroscopy is coupled with signal enhancement via plasmonic substrates, resulting in high sensitivity (down to single molecule)[12-13].

Raman microscopy can non-destructively identify a variety of different organic/inorganic chemical species because a molecule's Raman spectrum is a fingerprint-like representation of vibrational modes of chemical bonds present in the molecule[14,15,16]. Thus it provides very specific molecular identification that can be readily multiplexed and spectrally deconvoluted for the discrimination of specific signals in complex biological specimens. Raman microscopy can provide spatially resolved spectral images of whole microorganisms with micrometer resolution and very low water background[14].

According to an exemplary embodiment, a clinical sample (e.g., blood, sputum, urine, urinary catheter, subcutaneous injection port, surgically implanted medical device (i.e., orthopedic medical device, heart valve, cardiac pacemaker, implantable cardioverter defibrillator, etc.) or other medical device or part thereof) may be obtained and directly analyzed using RS without the need for initial or additional culturing of the sample. According to some embodiments, there is also no need for labeling of the sample prior to analysis. In this embodiment, QSMs are identified based on characteristic Raman scattering peaks in these spectra. The obtained sample is analyzed using RS to detect the presence of Raman scattering peaks associated with QSMs that are known biomarkers for pathogens of interest.

Figure 2:
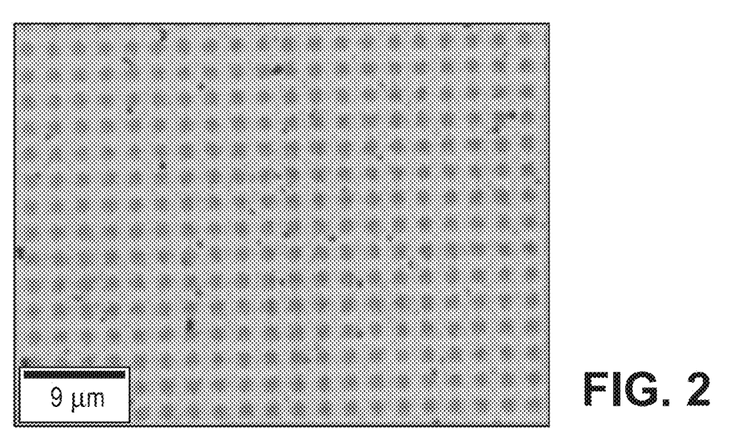
FIG. 2 is an optical image of silver grids formed using the laser-deposited methodologies described herein.

The Examples section below provides data obtained that developed parameters separation of simple QSM mixtures [gram negative bacterial QSMs C4-homoserine lactone (C4-HSL) and 3-oxo-C12-HSL; fungal QSM, farnesol] monitoring characteristic fragment ions by MS ('501, FIG. 2).

As previously described, RS observes inelastic scattering of incident photons that are characteristic of its interaction with a given material. RS can be significantly enhanced if the targeted molecule is close to nanosized noble metal surfaces such that locally excited surface plasmons in the metal surfaces interact strongly with the target molecule. This effect, known as Surface-Enhanced Raman Scattering (SERS), increases the sensitivity of the method by many orders of magnitude[17,18]. Thus, according to another embodiment, SERS can be used to obtain even more sensitive results than those obtained in RS.

According to a first SERS embodiment, a clinical sample (e.g., blood, sputum, urine, catheter tip or other medical device or part thereof) may be obtained and infused with pre-synthesized noble metal (e.g., silver or gold) nanoparticle colloids. This may be achieved, for example, by preparing a suspension of the clinical sample and a silver colloidal suspension using chemical reduction methods such as citrate or hydroxylamine hydrochloride reductions. Similar chemical reductions can be performed to analyze biofilms on glass, silicone, or other medical device surfaces.

According to another embodiment, metal nanoparticles (NP) can be patterned on glass to create SERS sensor arrays for Raman imaging. This approach is useful for detecting QSM analytes present as dissolved species in a fluid phase, such as a body fluid specimen. This approach has the advantage of including built in negative control regions, and allows facile creation of heterogeneous sensors that may be tailored to specific analytes. One or more parameters can be varied to produce a desired pattern. Examples of pattern variables include, but are not limited to, spot diameter, pitch, density of NP deposition, NP composition (photoreduction of $AgNO_3$ vs. $HAuCl_4$; may permit better tuning of SERS to available excitation sources) etc. Patterns can be characterized with light and electron preparing the sample for analysis via spectroscopy microscopy. SERS can be imaged from standards (i.e., pyridine and/or 2-mercaptoethanol) with Raman scattering.

According to an embodiment, the (prepared) sample is deposited on the SERS sensor and analyzed. QSMs (or other biomarkers) can be identified based on characteristic Raman scattering peaks in these spectra. According to some embodiments, the sample may be directly analyzed upon retrieval. According to other embodiments the sample may be placed in a buffer or other solution. According to still further embodiments, the sample may undergo some type of preparation intended to increase the concentration of analyte in the sample. Examples of such preparation may include, for example, chemical extraction and concentration or the use of a solid phase substrate with affinity for the analyte, which could concentrate and then release the analyte. It should be noted that this type of sample preparation is still significantly less time and labor consuming than traditional culture-based methodologies. However, as discussed above, the in clinical settings it is often important for the test to be as simple and fast as possible and thus the methods and apparatus described herein may make such additional sample preparation unnecessary.

As demonstrated in the Examples section below, we demonstrated an ability to acquire Raman spectra from pure gram-negative bacterial and fungal QSMs in confocal Raman imaging and SERS modalities.

According to another embodiment, the present disclosure proposes the in situ creation of a sample-SERS sensor complex formed by deposition of metal particles directly onto the sample being analyzed, such as a putatively colonized medical device, or even directly within a biofilm. According to an embodiment, formation of the SERS sensor may be performed using a photoreductive metal nanoparticle deposition method such as that described in A. Pinchuk[19]. Briefly, a medical device such as a catheter tip, is infused with a noble metal salt solution such as, but not limited to silver nitrate. A light source such as a laser is then directed towards the device in order to produce metal particles via photoreduction. Because the light source is provided as a focused laser beam, the metal particles can be formed in patterns, as demonstrated in the Examples section below. One advantage of the photoreductive technique is that it enables printing of SERS sensors not just on devices, but may be able to deposit sensors in situ, i.e., on or within biological samples including, for example, within biofilms, where analytes/pathogens are at their highest concentration.

Suitable noble metals include, for example, gold (AuNP), ruthenium (RuNP), rhodium (RhNP), palladium (PdNP), osmium (OsNP), iridium (IrNP), and platinum (PtNP). Accordingly, suitable noble metal salt solutions include solutions including salts formed of these noble metals.

Alternatively, rather than using a focused laser beam, a similar process may utilize an intense lamp-based illumination (UV or violet wavelengths). Of course, the lamp-based illumination technique would result in particle deposition happening everywhere, without specificity for deposition on a device or in a biofilm. Accordingly, if lamp-based illumination is used, it may be desirable for the device/biofilm etc. to be transferred to a new buffer after the deposition process and for the measurements to be taken in the new buffer.

An exemplary method for laser-induced deposition of silver nanoparticle (AgNP) patterns on glass is provided in the Examples section below. Of course it will be understood that such patterns could also be deposited on medical devices or within biofilms as described above. It will also be understood that similar methods can be used to prepare plasmonic surfaces composed of other noble metals, such as gold (AuNP), ruthenium (RuNP), rhodium (RhNP), palladium (PdNP), osmium (OsNP), iridium (IrNP), and platinum (PtNP).

According to yet another embodiment, laser-induced deposition may enable the deposition of metal particles within individual cells. In this example, the obtained sample is diluted in a metal salt solution and the silver, gold, or other metal noble ions are allowed to infuse into cellular structures and reduced by a focused laser spot to form metal nanoparticles. Plasmonically enhanced Raman signals could be observed from these locally produced intracellular nanoprobes, thereby enabling the detection of QSMs or other biomolecules inside cells. A major advantage of this detection method is that the formation of metal nanomaterials and the detection of Raman signals could occur at the same time.

Accordingly, in another embodiment, the present disclosure provides for an in situ SERS sensor in the form of noble metal nanoparticles deposited onto or into a clinical sample (e.g., blood, sputum, urine, catheter tip or other medical device or part thereof).

According to a still further embodiment, the noble metal nanoparticles that form the SERS sensor could be functionalized. According to various embodiments, the nanoparticles could be functionalized with selected molecules that could 1) target particles to the surfaces of fungi or bacterial cells and/or 2) bind directly to QSMs (or other biomarkers), thus concentrating them on plasmonic surfaces and enhancing sensitivity[20,21]. According to an exemplary embodiment, polypeptide based probes (whether synthesized in-house or commercially available) can be attached to noble metal nanoparticles by reacting those probes with a crosslinker. Suitable crosslinkers include, but are not limited to, thiol-PEG-NHS moieties which conjugate to primary amine groups, and then attached to particle surfaces via standard thiol chemistry. Other reactive groups that might be useful include, but are not limited to, carbodiimide, NHS ester, imidoester, maleimide, haloacetyl, pyridyldisulfide, hydrazide, alkoxyamine, diazirine, aryl azide, isocyanates. Alternatively, an arrangement commonly referred to as "click chemistry" could be used. In this arrangement, the reactive group is an azide or alkyne on the crosslinking reagent that reacts with either an alkyne or azide, respectively, on the probe. Of course it will be understood that while PEG is a commonly used linker, other water soluble polymer chains could be used.

For example, particle binding to fungi can be targeted by labeling particles with recombinant human Dectin-1, which binds beta-(1,3)-D-glucan, a polysaccharide that is present in fungi but absent from bacterial and human cells[22]. Particles can be targeted to gram-negative bacterial surfaces by decorating them with *Bacillus polymyxa* polymyxin B, a polypeptide that binds LPS components present in their outer membranes but absent from fungi and human membranes[23,24]. Alternatively, or additionally, lectins such as concanavalin A and wheat germ agglutinin which bind to bacterial surfaces and extracellular matrices produced by bacteria could be used to target bacteria.

As stated above, nanoparticles could alternatively or additionally be functionalized to enrich for QSM (or other biomarker) binding. For example, farnesol can be targeted for binding to plasmonic nanoparticles by conjugating particle surfaces with recombinant human Farnesoid X Receptor (rhFXR), a nuclear receptor that binds farnesol[25]. Similarly, acyl homoserine lactone QSMs can be targeted by attaching *Vibrio fischeri* LuxR, the classic gram-negative acyl homoserine lactone binding transcription factor[26], to plasmonic particles.

Of course, it will be appreciated that various combinations and sub-combinations of the methods described above could be used to enhance and enable identification of a wide variety of targets including, but not necessarily limited to the pathogens described herein.

It will be appreciated that in order for a methodology to be clinically appropriate, particularly in the area of diagnostics, the methodology must be able to discriminate between samples at a high level of confidence. As evidenced in the Examples section, the presently described methodology was able to image mixtures of analytes in a complex cellular background with spatial discrimination.

The present disclosure contemplates that a library of QSM (and other biomarkers detectable using the same or other detection mechanism) could be produced by culturing samples of suitable QSMs and other biomarkers and analyzing and recording, for example, the Raman scattering peaks that result from their presence using, for example, multivariate statistical methods for deconvolution of QSM and specimen background components in the data. The, for example, Raman scattering peaks that are obtained from analysis of a clinical sample could then be compared to the library to determine the presence of and identify pathogens in the clinical sample. These results could, in turn, then be used to determine treatment paths and options.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

1. Antibiotic resistance threats in the United States, 2013. In: (CDC) CfDCaP, editor. Atlanta, Ga. 2013.
2. Freifeld A G, Bow E J, Sepkowitz K A, Boeckh M J, Ito J I, Mullen C A, et al. Clinical practice guideline for the use of antimicrobial agents in neutropenic patients with cancer: 2010 update by the infectious diseases society of America. Clin Infect Dis. 2011; 52(4):e56-93. Epub 2011/01/25. doi: 10.1093/cid/cir073. PubMed PMID: 21258094.
3. McKenzie H, Hayes L, White K, Cox K, Fethney J, Boughton M, et al. Chemotherapy outpatients' unplanned presentations to hospital: a retrospective study. Supportive care in cancer: official journal of the Multinational Association of Supportive Care in Cancer. 2011; 19(7): 963-9. Epub 2010/05/26. doi: 10.1007/s00520-010-0913-y. PubMed PMID: 20499108.
4. Rosa R G, Goldani L Z. Cohort study of the impact of time to antibiotic administration on mortality in patients with febrile neutropenia. Antimicrobial agents and chemotherapy. 2014; 58(7):3799-803. Epub 2014/04/23. doi: 10.1128/AAC.02561-14. PubMed PMID: 24752269; PubMed Central PMCID: PMC4068526.
5. McGee D C, Gould M K. Preventing complications of central venous catheterization. The New England journal of medicine. 2003; 348(12):1123-33. Epub 2003/03/21. doi: 10.1056/NEJMra011883. PubMed PMID: 12646670.
6. Raad I. Intravascular-catheter-related infections. Lancet. 1998; 351(9106):893-8. Epub 1998/04/03. doi: 10.1016/S0140-6736(97)10006-X. PubMed PMID: 9525387.
7. Ruesch S, Walder B, Tramer M R. Complications of central venous catheters: internal jugular versus subclavian access—a systematic review. Critical care medicine. 2002; 30(2):454-60. Epub 2002/03/13. PubMed PMID: 11889329.
8. Yousif A, Jamal M A, Raad I. Biofilm-based central line-associated bloodstream infections. Advances in experimental medicine and biology. 2015; 830:157-79. Epub 2014/11/05. doi: 10.1007/978-3-319-11038-7_10. PubMed PMID: 25366227.
9. Kubryk P, Niessner R, Ivleva N P. The origin of the band at around 730 cm(-1) in the SERS spectra of bacteria: a stable isotope approach. The Analyst. 2016; 141(10): 2874-8. Epub 2016/05/04. doi: 10.1039/c6an00306k. PubMed PMID: 27136752.
10. Pahlow S, Meisel S, Cialla-May D, Weber K, Rosch P, Popp J. Isolation and identification of bacteria by means of Raman spectroscopy. Advanced drug delivery reviews. 2015; 89:105-20. Epub 2015/04/22. doi: 10.1016/j.addr.2015.04.006. PubMed PMID: 25895619.
11. Knauer M, Ivleva N P, Niessner R, Haisch C. Optimized surface-enhanced Raman scattering (SERS) colloids for the characterization of microorganisms. Analytical sciences: the international journal of the Japan Society for Analytical Chemistry. 2010; 26(7):761-6. Epub 2010/07/16. PubMed PMID: 20631436.
12. Basuray S, Pathak A, Bok S, Chen B, Hamm S C, Mathai C J, et al. Plasmonic nano-protrusions: hierarchical nanostructures for single-molecule Raman spectroscopy. Nanotechnology. 2017; 28(2):025302. Epub 2016/12/03. doi: 10.1088/0957-4484/28/2/025302. PubMed PMID: 27905323.
13. Lee H M, Jin S M, Kim H M, Suh Y D. Single-molecule surface-enhanced Raman spectroscopy: a perspective on the current status. Physical chemistry chemical physics: PCCP. 2013; 15(15):5276-87. Epub 2013/03/26. doi: 10.1039/c3cp44463e. PubMed PMID: 23525118.
14. Ivleva N P, Wagner M, Szkola A, Horn H, Niessner R, Haisch C. Label-free in situ SERS imaging of biofilms. The journal of physical chemistry B. 2010; 114(31): 10184-94. Epub 2010/08/06. doi: 10.1021/jp102466c. PubMed PMID: 20684642.
15. Zaleski S, Clark K A, Smith M M, Eilert J Y, Doty M, Van Duyne R P. Identification and Quantification of Intravenous Therapy Drugs Using Normal Raman Spectroscopy and Electrochemical Surface-Enhanced Raman Spectroscopy. Analytical chemistry. 2017; 89(4):2497-504. Epub 2017/02/15. doi: 10.1021/acs.analchem.6b04636. PubMed PMID: 28192951.
16. Bonnier F, Byrne H J. Understanding the molecular information contained in principal component analysis of vibrational spectra of biological systems. The Analyst. 2012; 137(2):322-32. Epub 2011/11/25. doi: 10.1039/c1an15821j. PubMed PMID: 22114757.
17. Jeon T Y, Kim D J, Park S G, Kim S H, Kim D H. Nanostructured plasmonic substrates for use as SERS sensors. Nano convergence. 2016; 3(1):18. Epub 2017/

18. Kim D, Campos A R, Datt A, Gao Z, Rycenga M, Burrows N D, et al. Microfluidic-SERS devices for one shot limit-of-detection. The Analyst. 2014; 139(13):3227-34. Epub 2014/04/24. doi: 10.1039/c4an00357h. PubMed PMID: 24756225; PubMed Central PMCID: PMC4067008.
19. Ivleva N P, Wagner M, Horn H, Niessner R, Haisch C. Raman microscopy and surface-enhanced Raman scattering (SERS) for in situ analysis of biofilms. Journal of biophotonics. 2010; 3(8-9):548-56. Epub 2010/07/01. doi: 10.1002/jbio.201000025. PubMed PMID: 20589769.
20. Lee H, Odom T W. Controlling ligand density on nanoparticles as a means to enhance biological activity. Nanomedicine (Lond). 2015; 10(2):177-80. Epub 2015/01/21. doi: 10.2217/nnm 14.204. PubMed PMID: 25600963.
21. Camden J P, Dieringer J A, Zhao J, Van Duyne R P. Controlled plasmonic nanostructures for surface-enhanced spectroscopy and sensing. Accounts of chemical research. 2008; 41(12):1653-61. Epub 2008/07/18. doi: 10.1021/ar800041s. PubMed PMID: 18630932.
22. Williams D L. Overview of (1→3)-beta-D-glucan immunobiology. Mediators of inflammation. 1997; 6(4):247-50. Epub 1997/01/01. doi: 10.1080/09629359791550. PubMed PMID: 18472852; PubMed Central PMCID: PMC2365860.
23. Falagas M E, Kasiakou S K. Colistin: the revival of polymyxins for the management of multidrug-resistant gram-negative bacterial infections. Clin Infect Dis. 2005; 40(9):1333-41. Epub 2005/04/13. doi: 10.1086/429323. PubMed PMID: 15825037.
24. Landy M, Rosenman S B, Warren G H. An antibiotic from *Bacillus subtilis* active against pathogenic fungi. J Bacteriol. 1947; 54(1):24. Epub 1947/07/01. PubMed PMID: 20255120.
25. Forman B M, Goode E, Chen J, Oro A E, Bradley D J, Perlmann T, et al. Identification of a nuclear receptor that is activated by farnesol metabolites. Cell. 1995; 81(5): 687-93. Epub 1995/06/02. PubMed PMID: 7774010.
26. Urbanowski M L, Lostroh C P, Greenberg E P. Reversible acyl-homoserine lactone binding to purified *Vibrio fischeri* LuxR protein. J Bacteriol. 2004; 186(3):631-7. Epub 2004/01/20. PubMed PMID: 14729687; PubMed Central PMCID: PMC321501.
27. J-F. Bryche, R. Gilibert, G. Barbillon, P. Gogol, J. Moreau, M. L. de la Chapelle, B. Bartenlian and M. Canva, Plasmonics. 11, 601 (2016).
28. J. Fontana, J. Livenere, F. J. Bezares, J. D. Caldwell, R. Rendell and B. R. Ratna, Appl. Phys. Lett. 102, 201606 (2013).
29. J. D. Caldwell, O. Glembocki, F. J. Bezares, N. D. Bassim, R. W. Rendell, M. Feygelson, M. Ukaegbu, R. Kasica, L. Shirey and C. Hosten, ACS Nano. 5, 4046 (2011).
30. J-F. Bryche, R. Gilibert, G. Barbillon, M. Sarkar, A-L. Coutrot, F. Hamouda, A. Aassime, J. Moreau, M. L. de la Chapelle, B. Bartenlian and M. Canva, J. Mater. Sci. 50, 6601 (2015).
31. J. Y. Gui, D. A. Stern, D. G. Frank, F. Lu, D. C. Zapien and A. T. Hubbard, Langmuir. 7, 955 (1991).
32. Y. Guo, M. K. K. Oo, K. Reddy and X. Fan, ACS Nano. 6, 381 (2012).
33. W. F. Pearman, M. Lawrence-Snyder, S. M. Angel and A. W. Decho, Appl. Spectroscopy. 61, 1295 (2007).
34. A. Claussen, S. Abdali, R. W. Berg, M. Givskov and T. Sams, Curr. Phys. Chem. 3, 199 (2013).
35. S. Magill et al., "Multistate point-prevalence survey of health care-associated infections.," N. Engl. J. Med. 27(370), 1198-1208 (2014).
36. N. Yapar, "Epidemiology and risk factors for invasive candidaiasis," J. Ther. Clin. risk Manag. 10, 95-105 (2014).
37. S. R. Lockhart, "Current Epidemiology of *Candida* Infection.," Clin. Microbiol. Newsl. 36(17), 131-136 (2014).
38. M. Pfaller and D. Diekema, "Epidemiology of invasive candidiasis: a persistent public health problem.," Clin. Microbiol. Rev. 20(1), 133-163 (2007).
39. O. Gudlaugsson et al., "Attributable mortality of nosocomial candidemia, revisited.," Clin. Infect. Dis. 37(9), 1172-1177 (2003) [doi:10.1086/378745].
40. F. G. De Rosa et al., "Invasive candidiasis and candidemia: new guidelines.," Minerva Anestesiol. 75(7-8), 453-458 (2009).
41. R. P. Wenzel and M. B. Edmond, "The impact of hospital-acquired bloodstream infections," Emerg. Infect. Dis. (7), 174-177 (2001).
42. M. Morrell, V. Fraser, and M. Kollef, "Delaying the Empiric Treatment of *Candida* Bloodstream Infection until Positive Blood Results are Obtained: a Potential Risk Factor for Hospital Mortality," Antimicrob. Agents Chemother. 49(9), 3640-3645 (2005).
43. K. Garey et al., "Time to Initiation of Flucanazole Therapy Impacts Mortality in Patients with Candidemia: A Multi-Institutional Study," Clin. Infect. Dis. 43(1), 25-31 (2006).
44. M Kami et al., "Effect of fluconazole prophylaxis on fungal blood cultures: An autopsy-based study involving 720 patients with haematological malignancy," Br. J. Haematol. 117(1), 40-46 (2002) [doi:10.1046/j.1365-2141.2002.03414.x].
45. J. Berenguer et al., "Lysis-centrifugation blood cultures in the detection of tissue-proven invasive candidiasis disseminated versus single-organ infection.," Diagnostic Microbiol. Infect. Dis. 17(2), 102-109 (1993).

Example I—Creation of SERS Sensors

Figure 1:
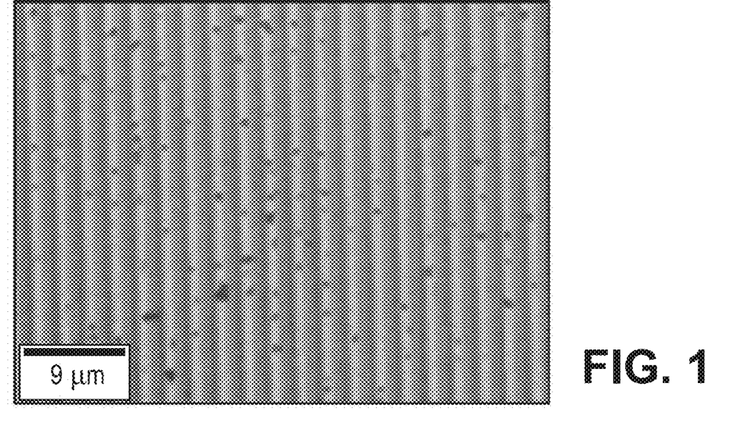
FIG. 1 is an optical image of silver wires formed using the laser-deposited methodologies described herein.
Figure 3:
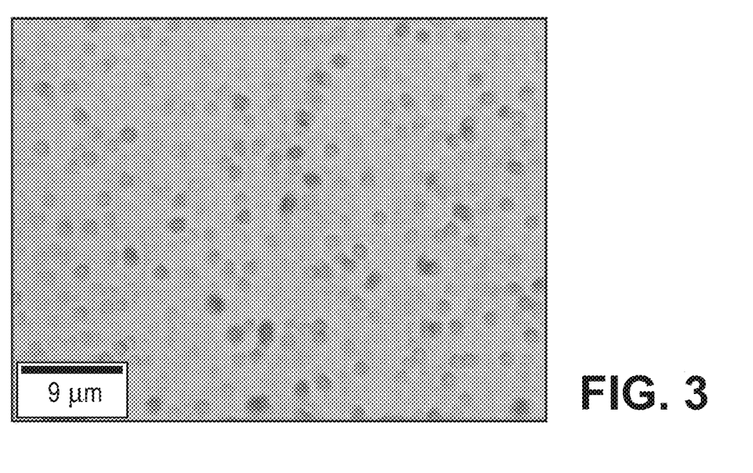
FIG. 3 is an optical image of a continuous film formed using the laser-deposited methodologies described herein.

In a laser-deposition process, aqueous solutions of AgNO3 (2 mM) and sodium citrate (100 mM) were mixed at a 1:1 molar ratio. The mixture was then dropped onto a glass cover slip which was mounted on a Leica TCS SP5 confocal laser scanning microscope. A 405 nm wavelength diode laser (7 mW) was employed to deposit silver nanostructures at the liquid-substrate interface using a 10× objective lens (NA=0.25). Parameters for the confocal microscope were tuned so that the deposition resulted in a 1 mm×1 mm square consisting of the silver nanostructures. The deposited pattern can be pre-designed by varying parameters in the instrument's software. For example, an array of silver wires (as shown in FIG. 1 can be produced by using a lower resolution of deposition (i.e. 64×64 lines in a given area), while a continuous film (as shown in FIG. 3) can be made by a high resolution (i.e. 256×256 in a given area). The grid pattern shown in FIG. 2 was made by depositing an array of wires first, then repeating the same process with the laser beam path tuned by 90°.

After the deposition process was completed, the substrates were air dried after being washed with deionized (D.I.) water to remove excessive precursor chemicals. For enhancement factor estimations, typically 0.1 mM solution of thiophenol in ethanol was prepared and dropped onto the laser-deposited silver nanostructures. After a 2 h soaking period, the substrate was washed thoroughly with ethanol and dried. For the measurements of SERS from N-butyryl-L-homoserine lactone, an aqueous solution of the target molecule (0.1 mM) was placed on the dry laser-deposited silver nanostructures and directly measured by the Raman spectroscopy.

Morphology of the laser-deposited silver structures was characterized by using the Atomic Force Microscopy (AFM) mode in a Nearfield Scanning Optical Microscope (NSOM, Alpha300, Witec). The absorption spectra were acquired by an optical spectrometer (HR4000, Ocean Optics) using a high-power Xenon lamp (HPX-2000, Ocean Optics). Raman spectra of thiophenol (Sigma-Aldrich) and N-butyryl-L-homoserine lactone (Cayman Chemical Company) were acquired through Raman mode in the NSOM utilizing a Nd-YAG laser (532 nm) and 20× objective lens (NA=0.4). The acquisition time was fixed to 10 s.

To compare the SERS efficiency of the laser-deposited silver nanostructures to those of other relevant substrates, we evaluated the Enhancement Factor (EF) using thiophenol as a model molecule. Thiophenol has been widely used to evaluate the EF of noble metal nanomaterials due to its simple chemical structures and strong affinity to noble metal surfaces[27-30]. This affinity enables the formation of a stable self-assembled monolayer, which is advantageous to the precise measurement of the surface's EF. Before SERS measurements, a 0.1 mM solution of thiophenol in ethanol was prepared and dropped onto laser-deposited silver nanostructures. After a 2 h soaking period, the substrate was then washed thoroughly with ethanol and dried. The EF was estimated using the following equation:

$$EF = \frac{I_{SERS}}{N_{SERS}} / \frac{I_{Raman}}{N_{Raman}} \quad (1)$$

Where $I_{SERS}$ and $I_{Raman}$ are the measured Raman intensities for SERS and normal Raman spectroscopy, respectively. $N_{SERS}$ is the number of thiophenol molecules in the detection volume, which can be calculated as:

$$N_{SERS} = N_A \times \sigma_{surf} \times S \quad (2)$$

where $N_A$ is Avogadro's number, S is the area of collection, and $\sigma_{surf}$ is the surface coverage of thiophenol which is approximately 0.544 nmol/cm$^2$ [31].
$N_{Raman}$ in Equation (1) can be calculated as:

$$N_{Raman} = N_A \times C \times V \quad (3)$$

where C is the concentration of thiophenol (1 M), and V is the scattering volume which was calculated based on a method reported previously[32]. Specifically, the diameter of laser spot was about 4 μm and the collection depth was approximately 140 μm. Assuming that the illuminated cross-sectional area remains the same along the focal spot, the total effective detection volume was approximately 1.76 pL.

Figure 4:
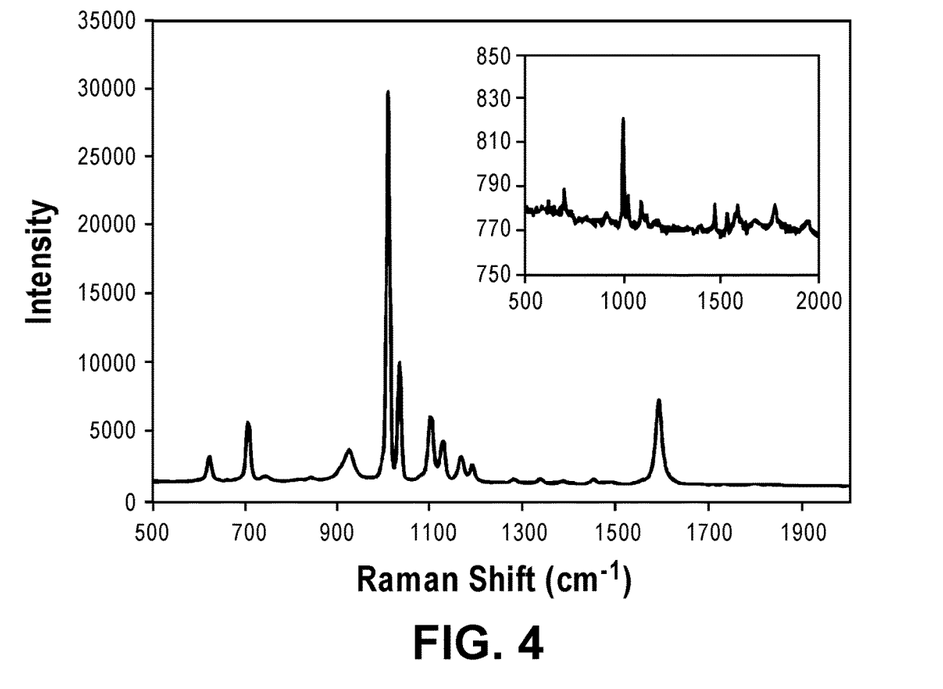
FIG. 4 shows the SERS spectrum of thiophenol on a laser-deposited silver nanostructure. The inset shows normal Raman spectrum of thiophenol (1 M), where the molecule was not attached to a metal deposit.

The strongest signature stretching mode at 1005 cm-1 was used in the calculation of the EF, as shown in FIG. 4. With the SERS intensity 36 times higher than that of the normal intensity, the EF was calculated to be 9.27×10$^5$. Although this result seems minimal when compared to EFs reported using gold nanodisks[30] or nanopillar arrays[29], these fabrication techniques can be expensive and time-consuming. Alternatively, the laser deposition technique offers a straightforward and cost-effective method to produce noble metal nanostructures with useful SERS efficiencies.

Figure 5:
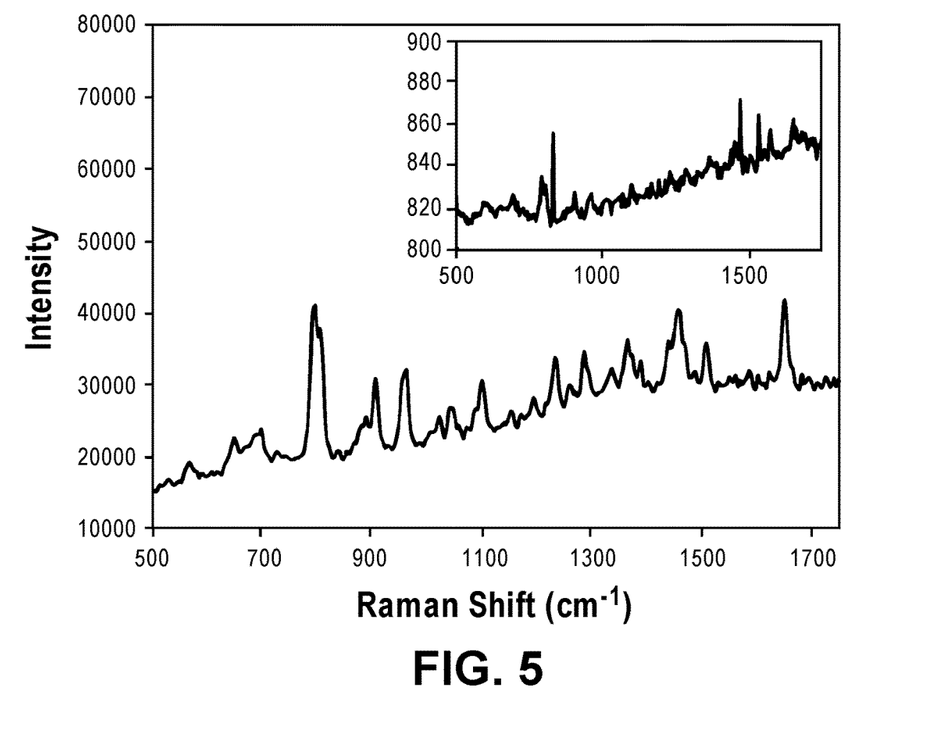
FIG. 5 shows the SERS spectrum of N-butyryl-L-homoserine lactone on a laser-deposited silver nanostructure. The inset shows normal Raman spectrum of N-butyryl-L-homoserine lactone (0.1 mM), where the molecule was not attached to a metal deposit.
Figure 6:
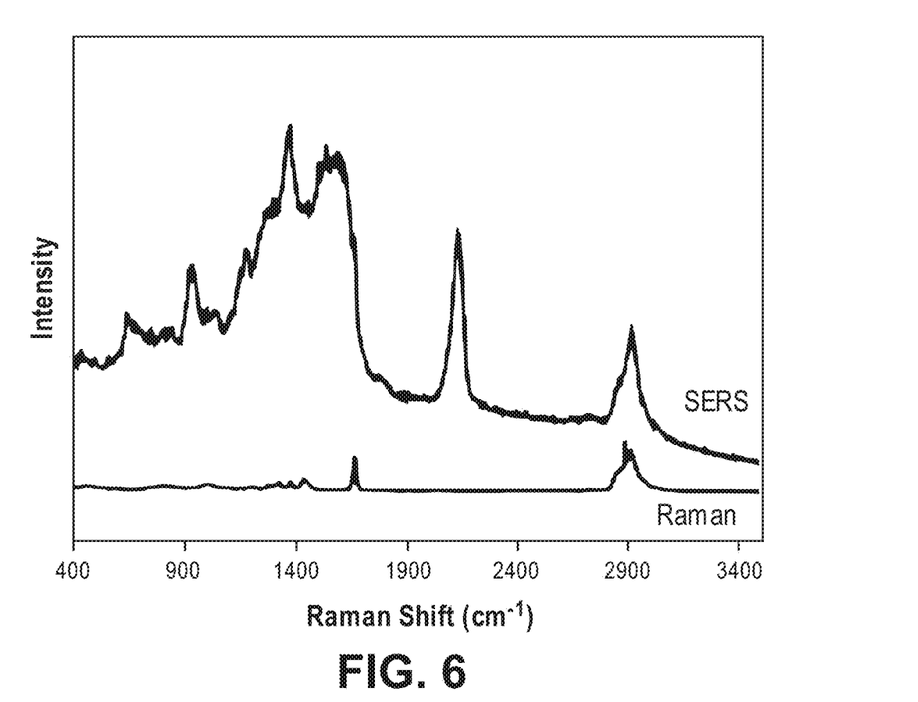
FIG. 6 shows SERS and Raman spectra of squalene using pre-fabricated silver nanostructures as the SERS substrate.
Figure 7:
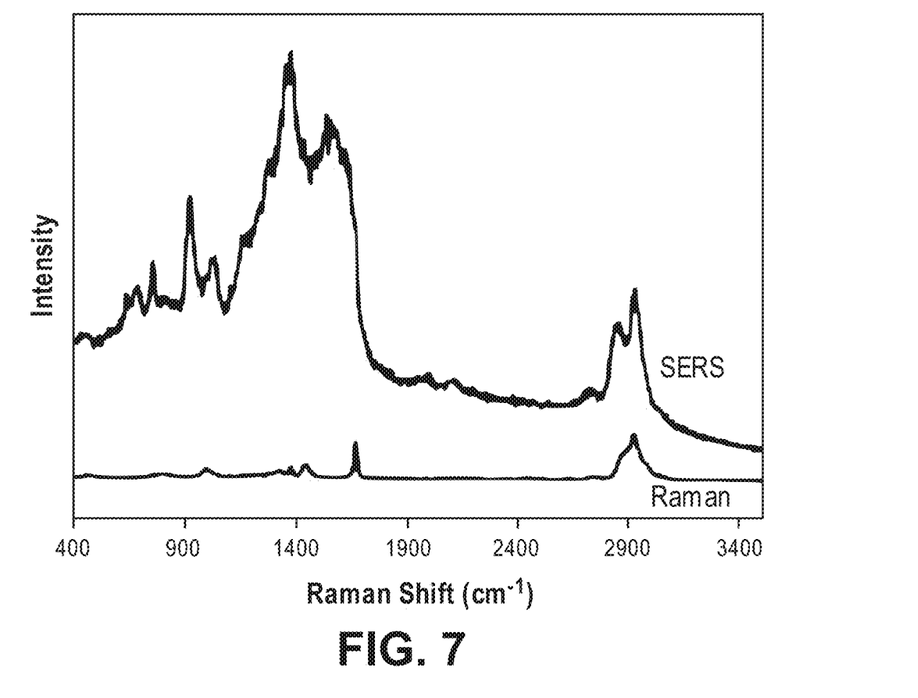
FIG. 7 shows SERS and Raman spectra of farnesol using pre-fabricated silver nanostructures as the SERS substrate.
Figure 8:
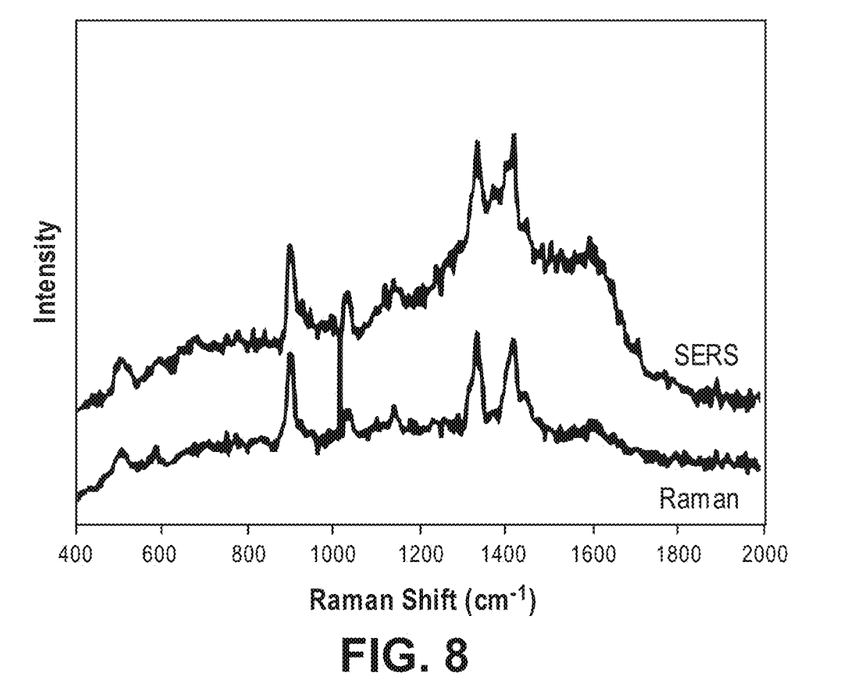
FIG. 8 shows SERS and Raman spectra of glycine using pre-fabricated silver nanostructures as the SERS substrate.
Figure 9:
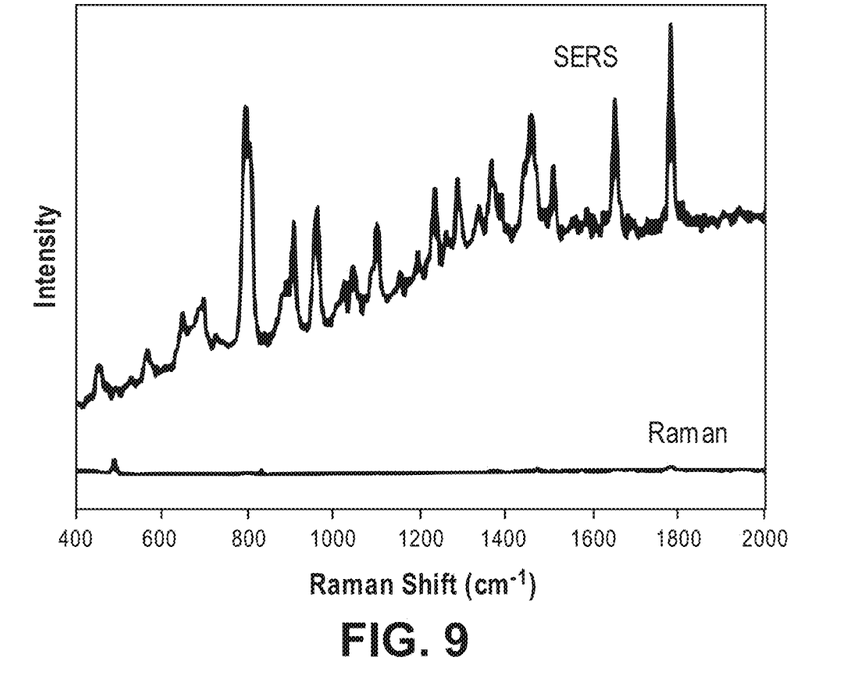
FIG. 9 shows SERS and Raman spectra of N-butyryl-L homoserine lactone using pre-fabricated silver nanostructures as the SERS substrate.
Figure 10:
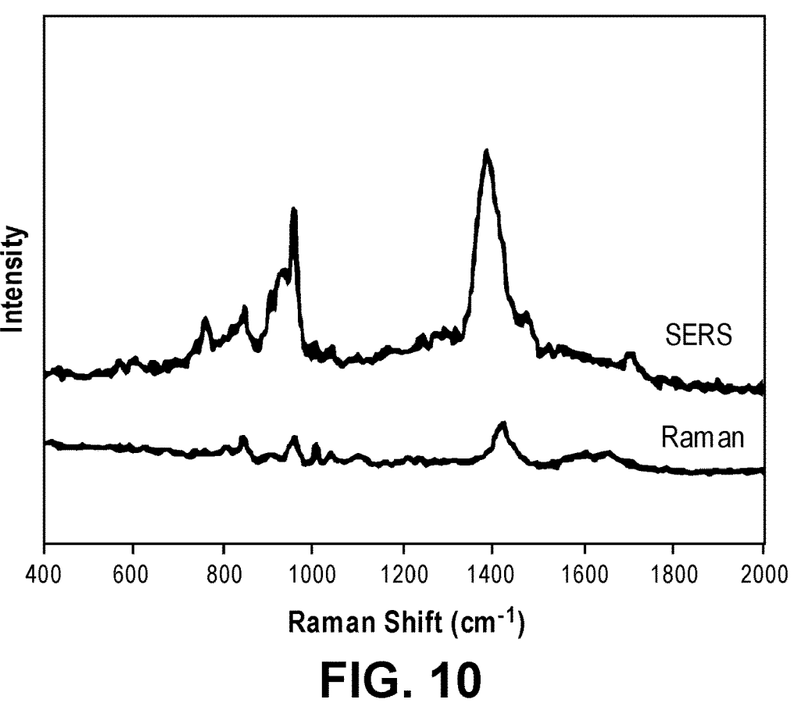
FIG. 10 shows SERS and Raman spectra of trisoldium citrate using silver nanoparticles formed by in situ laser-induced photoreduction.

FIG. 5 shows the SERS spectrum of N-butyryl-L-homoserine lactone (0.1 mM) once placed on the laser-deposited silver nanostructures. The amide I (1653 cm$^{-1}$), amide II (1508 cm$^{-1}$), amide III (1285 cm$^{-1}$), and amide IV (795 cm$^{-1}$) bands are clearly visible as compared to those in its normal Raman spectrum (FIG. 5 inset). Previous studies have shown that colloidal silver nanoparticles can be applied to measure quorum sensing molecules with detection limits down to 10-9 M[33,34]. In our study, because Raman signals are only enhanced when the target molecules are close enough to the surface of silver films, the sensitivity of SERS may be lower than those of using nanoparticle suspensions. However, one key advantage that the laser deposited structures offer is the reusability of both the analyte and the SERS substrate. This is particularly crucial for continuous and reproducible Raman measurements.

Example II—QSM Detection by RS and SERS

FIGS. 6-10 show SERS and normal Raman spectra of a series of microbial small molecules presented either on or off laser-deposited silver nanostructures, respectively, using the methods and apparatus described herein. The small molecules are: (FIG. 6) squalene (2 mg/mL), (FIG. 7) farnesol (2 mg/mL), (FIG. 8) glycine (10 mg/mL), (FIG. 9) N-butyryl-L-homoserine lactone (0.1 mM), and (FIG. 10) sodium citrate.

Figure 11:
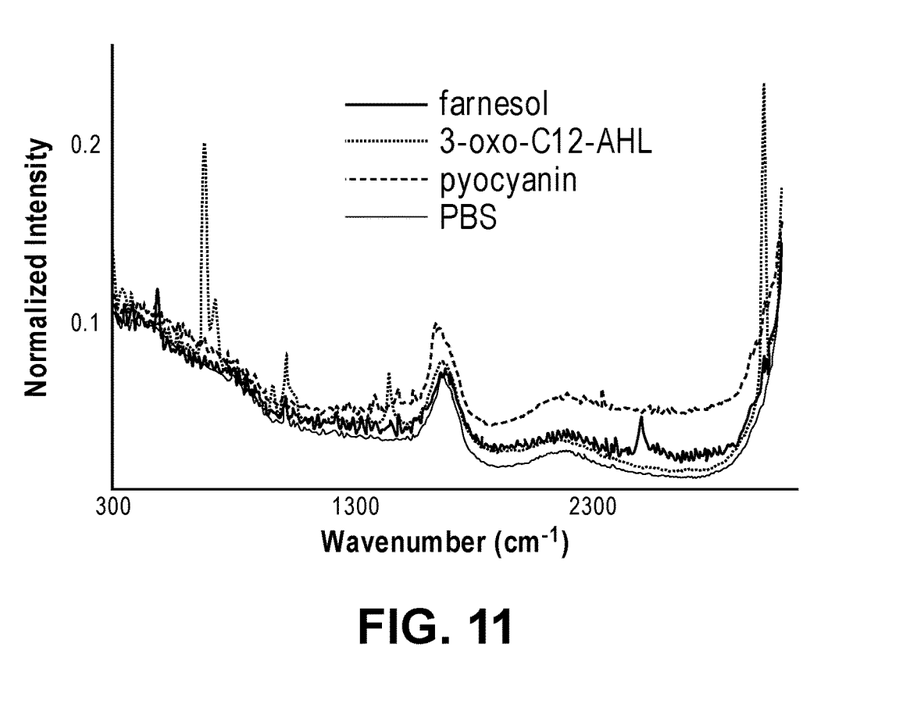
FIG. 11 shows Raman spectra of farnesol, 3-oxo-C12-AHL, pyocyanin, and PBS attained using the methods described herein.

FIG. 11 shows Raman spectra of Farnesol, 3-oxo-C12-AHL, Pyocyanin, and PBS attained using the methods described herein.

Example III

Figure 12:
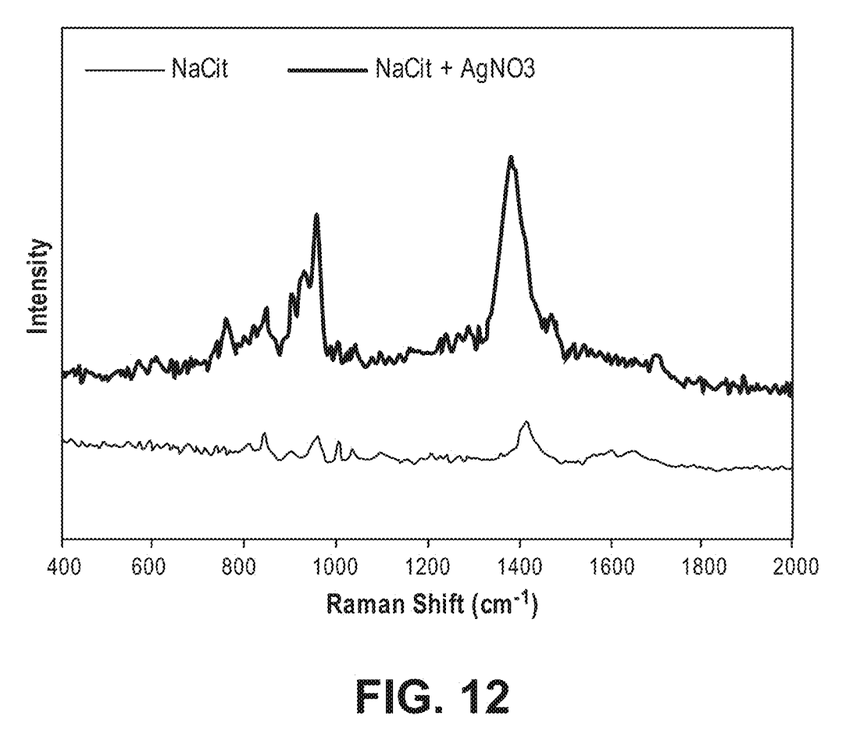
FIG. 12 shows the Raman spectrum of aqueous sodium citrate compared to the SERS spectrum when $AgNO_3$ was added and the mixture exposed to laser for 2 second before acquiring Raman signals.

In FIG. 12, Normal Raman spectra (blue line) was acquired firstly using a sodium citrate solution (1 M), then a AgNO3 solution (5 mM) was added at a 1:1 molar ratio (AgNO3:sodium citrate). After exposure to a 532 nm laser for 2 s, silver nanoparticles were formed in-situ at the focal plane by the photoreduction reaction, and the Raman signals of surrounding sodium citrate molecules were significantly enhanced by nanoparticles (red line). This result indicated that, as compared to pre-deposited silver nanostructures, locally formed silver nanoparticles could also be used as an effective SERS substrate.

What is claimed is:
1. A method for rapid, culture free pathogen detection comprising:
   obtaining a sample suspected of containing a pathogen,
   preparing the sample for analysis via Raman Spectroscopy (RS) or Surface Enhanced Raman Spectroscopy (SERS) using laser induced photoreduction and deposition of a metal salt to create a sample-sensor complex;
   analyzing the sample via RS or SERS to obtain a spectrum;
   comparing the obtained spectrum to a known spectrum which indicates the presence of the pathogen; and
   determining whether the sample contains the pathogen based on the comparison of the obtained spectrum to the known spectrum.
2. The method of claim 1 wherein the spectroscopy is Surface Enhanced Raman Spectroscopy (SERS).
3. The method of claim 2 wherein the known spectrum is the spectrum produced by one or more biomarkers for the pathogen.
4. The method of claim 3 wherein the biomarkers are Quorum Sensing Molecules (QSMs).

5. The method of claim 2 wherein the sample comprises a medical device.

6. The method of claim 2 wherein the sample comprises a biofilm.

7. The method of claim 6 wherein the SERS sensor is formed within the biofilm.

8. The method of claim 2 wherein the sample comprises cells and the SERS sensor is formed within the cell.

9. A method for preparing a sample for Surface Enhanced Raman Spectroscopy (SERS) comprising:
   exposing the sample to a noble metal salt solution; and
   directing a light source to at least a portion of the sample to photoreduce the noble metal thereby producing noble metal particles so as to produce a sample-SERS sensor complex.

10. The method of claim 9 wherein the sample comprises a medical device.

11. The method of claim 9 wherein the sample comprises a biofilm and the SERS sensor complex is formed within the biofilm.

12. The method of claim 9 wherein the sample comprises cells and the SERS sensor is formed within the cell.

* * * * *